(12) United States Patent
Yunusov et al.

(10) Patent No.: US 7,488,501 B2
(45) Date of Patent: Feb. 10, 2009

(54) ENZYMATIC PROCESS FOR GENERATION OF FOODS, FEEDSTUFFS AND INGREDIENTS THEREFOR

(75) Inventors: Temur Yunusov, College Station, TX (US); Steven R. Gregory, College Station, TX (US)

(73) Assignee: The Texas A&M University System, College Station, TX (US)

(*) Notice: Subject to any disclaimer, the term of this patent is extended or adjusted under 35 U.S.C. 154(b) by 829 days.

(21) Appl. No.: 10/618,023

(22) Filed: Jul. 11, 2003

(65) Prior Publication Data

US 2004/0058051 A1 Mar. 25, 2004

Related U.S. Application Data

(60) Provisional application No. 60/395,692, filed on Jul. 12, 2002.

(51) Int. Cl.
*A23L 1/00* (2006.01)
(52) U.S. Cl. .......................... 426/49; 426/52; 426/615; 426/656; 426/661
(58) Field of Classification Search .................. 426/18, 426/49, 50, 51, 52, 590, 615, 618, 656, 661
See application file for complete search history.

(56) References Cited

U.S. PATENT DOCUMENTS

| 4,282,319 | A | 8/1981 | Conrad | |
|---|---|---|---|---|
| 4,927,649 | A | 5/1990 | Antenucci | |
| 6,703,227 | B2 * | 3/2004 | Jakel et al. | 435/72 |
| 6,709,848 | B1 * | 3/2004 | Martin et al. | 435/134 |
| 6,890,572 | B2 * | 5/2005 | Kragh et al. | 426/28 |

FOREIGN PATENT DOCUMENTS

| EP | 0 350 952 B1 | 1/1990 |
|---|---|---|
| EP | 0 479 596 B1 | 4/1992 |
| GB | 1 395 967 A | 5/1975 |
| GB | 1 465 396 A | 2/1977 |

* cited by examiner

*Primary Examiner*—Leslie Wong
(74) *Attorney, Agent, or Firm*—Bracewell & Giuliani LLP

(57) ABSTRACT

A method for processing organic materials into highly soluble food products is provided by treating the organic material with one enzyme at pH and temperature conditions optimal for reaction followed by a condition change to inactivate the first enzyme while creating an optimal condition for a second enzyme and further terminating the second reaction by inactivating the second enzyme. A third enzyme may optionally be added to this reaction. The sequential enzyme-treated products are then cooled, filtered and dried thereby transformed into final food products.

18 Claims, 2 Drawing Sheets

ENZYMATIC PROCESS FOR GENERATION OF FOODS, FEEDSTUFFS AND INGREDIENTS THEREFOR

CROSS-REFERENCE TO RELATED APPLICATION

This application is a non-provisional patent application which claims priority of provisional application U.S. Patent Application No. 60/395,692, filed on Jul. 12, 2002.

BACKGROUND OF THE INVENTION

1. Field of the Invention

The present invention relates to the field of food processing and, more particularly, to an enzymatic process for generation of foods, feedstuffs and ingredients therefor from organic materials.

2. Description of Related Art

Nutritional value of all natural food sources is determined by three main factors: chemical composition, digestibility of main components including bioavailability for humans, and functional properties of both initial food sources and their components. Organic materials are routinely processed into food products in food processing industry. For example, amaranth grain is processed and transformed into high-protein flour and maltodextrins mixture (Process Biochemistry, Vol. 29, 1994, pp. 289-293). The resultant flour contains 10.7% crude fiber and 30.9% protein. With such significant amount of crude fiber content, the flour would have restrictions related to both dietary and functional properties.

The purpose of the invention is to develop a method for processing organic materials into highly soluble and nutritional food products with increased dietary and functional properties of grain components.

SUMMARY OF THE INVENTION

With the foregoing in mind, the present invention advantageously provides a method for processing organic materials (for example, grains) into foods, feedstuffs and food ingredients. Preferably, this process includes steps of applying a sequence of two or more enzymes to solubilize nutrients into water for a food or feed ingredient. Further preferably, this process may also include steps of removing fat from candidate grain(s), oilseeds and biomass waste and then transforming the defatted material into a ready-to-use protein/carbohydrate food product or specialty ingredient precursor. This has immediate value to food companies who are targeting nutritional markets such as for allergic populations, elderly populations and infant populations (e.g., infant formula, and/or digestive disorder supplements). This creates a new tool for providing food products with superior nutrition and high digestibility. Additionally, this method allows broadening of functional properties of components so as to open opportunities for diverse applications for new food products including diet and herbal destinations. Also, the cost effectiveness of the food processing and value of the food products are increased significantly.

Particularly, the invention advantageously provides a method for processing organic materials in an aqueous solution into food products by using sequential enzyme treatment. Preferably, this method may include sequential enzyme treatment following a step of fat removal from the materials. For certain grains, a protease (e.g., neutrase) is first mixed with the organic materials and then, after an increase in temperature, an alpha-amylase (e.g., termamyl) is added to convert the starch to a soluble state. For certain oilseeds, a glycosidase (e.g., viscozyme) is first mixed with the organic materials and then, after pH is increased, a protease (e.g., neutrase) is added to convert the protein into a soluble state. For certain blends of grains and oilseeds, a glycosidase (e.g., viscozyme) is first mixed with the organic materials and then, after pH is increased, a protease (e.g., neutrase) is added to convert the protein into a soluble state. And then the temperature is increased to deactivate the protease. An alpha-amylase (e.g., termamyl) is thereafter added to convert the starch to a soluble state.

Specifically, there is provided a process for solubilizing an organic material in an aqueous solution. This process advantageously includes treating the organic material with a protease at a temperature effective to maintain the protease active; modifying the temperature to a level effective to deactivate the protease; treating the organic material with an alpha-amylase, the alpha-amylase being effective at the modified temperature; and modifying the temperature to a level effective to deactivate the alpha-amylase. This process is beneficial for organic materials high in starch (e.g., grains).

There is provided another process for solubilizing an organic material in an aqueous solution. This process advantageously includes treating the organic material with a glycosidase at a pH and a temperature effective to maintain the glycosidase active; modifying the pH to a level effective to deactivate the glycosidase; treating the organic material with a protease, the protease being effective at the modified pH; and modifying the temperature to a level effective to deactivate the protease. This process is beneficial for organic materials low in starch but high in muscilage (e.g., certain oilseeds).

There is provided still another process for solubilizing an organic material in an aqueous solution. This process advantageously includes treating the organic material with a glycosidase at a pH and a temperature effective to maintain the glycosidase active; modifying the pH to a level effective to deactivate the glycosidase; treating the organic material with a protease, the protease being effective at the modified pH; modifying the temperature to a level effective to deactivate the protease; treating the organic material with an alpha-amylase, the alpha-amylase being effective at the modified temperature and pH; and further modifying the temperature to a level effective to deactivate the alpha-amylase. This process is beneficial for organic materials high in both starch and muscilage (e.g., certain oilseed and grain mixes).

BRIEF DESCRIPTION OF THE DRAWING

Some of the features, advantages, and benefits of the present invention having been stated, others will become apparent as the description proceeds when taken in conjunction with the accompanying drawings in which.

DETAILED DESCRIPTION OF THE INVENTION

Figure 1:
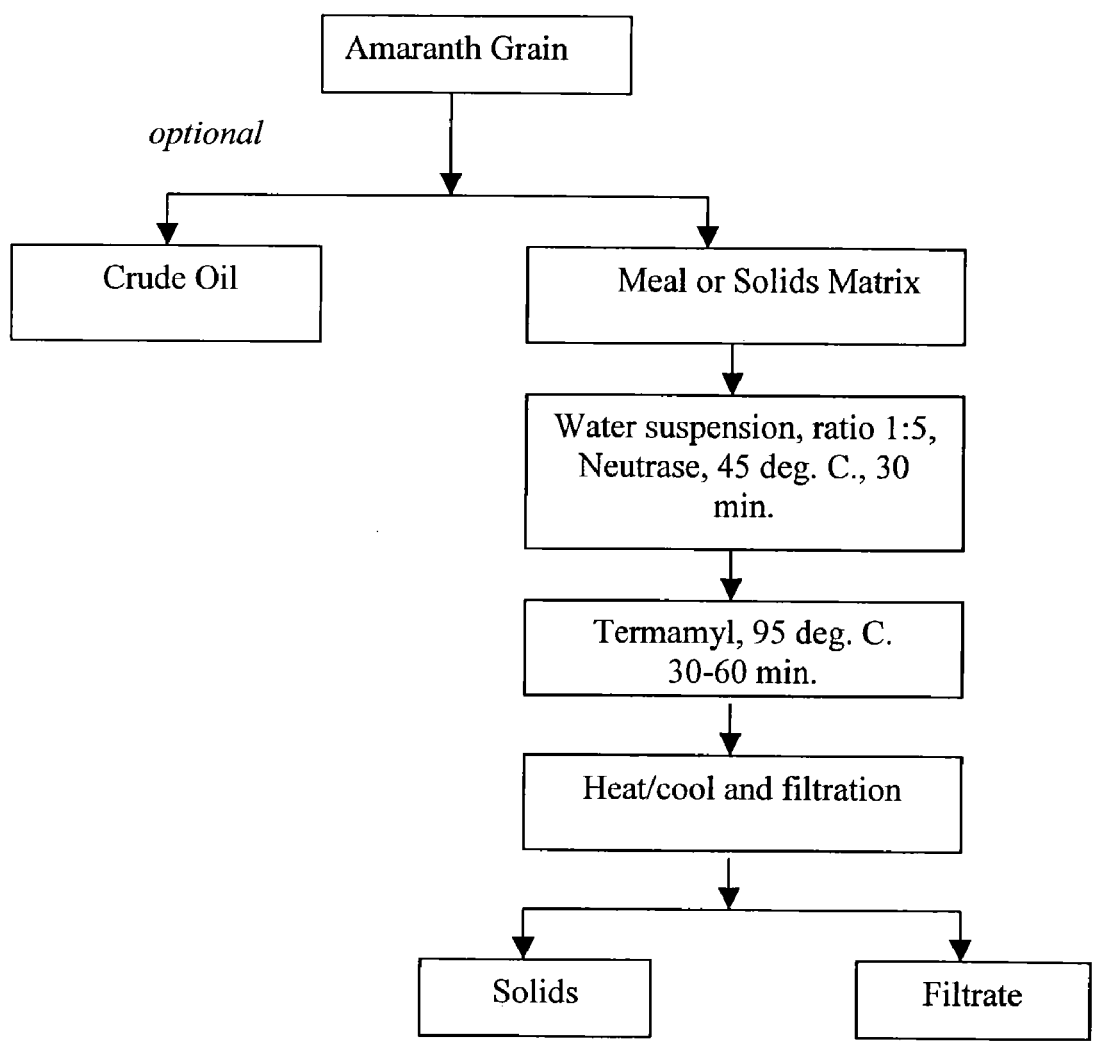
FIG. 1 is a flow chart demonstrating the method for processing amaranth grain into highly soluble foods, feedstuffs and/or food ingredients according to the present invention.

The present invention will now be described more fully hereinafter with reference to the accompanying drawings which illustrated preferred embodiments of the invention. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art.

The present invention is directed to a method of processing organic materials for high quality oil, proteins and soluble starch or a mixture of several components as food ingredients using sequential enzymes and appropriate conditions, (i.e., temperature, time). Preferably, organic materials, for example, amaranth grains, are first defatted using a conventional method and the defatted grains are subsequently transformed into highly soluble (digestible) protein and starch fraction using a sequential enzyme, temperature, and time protocol.

The innovation of the method is to remove or extract oil from an organic matrix by conventional methods and subsequently generate good yields of highly soluble food products. The temperature ranges that are suitable for this invention include temperatures suitable for the breakdown of proteins and carbohydrates by neutrase and temperatures that are effective for deactivating neutrase. The temperature and processing times reflect those determined to meet the processing goal while at the same time producing a palatable product. Flavor and quality of the resultant solid food product depends on stopping the process prior to imparting a bitter or otherwise undesirable taste.

This invention allows for thorough solubilization of the protein and starch found in starting raw materials. Existing technology only allows for partial solubilization of protein and starch, thereby wasting valuable nutrients. The invention uses a sequence of two or three enzyme classes to process organic materials into food products. In one preferred embodiment, protease is followed by alpha-amylase treatment. In another embodiment, glycosidase is followed by protease treatment and possibly further followed by alpha-amylase treatment. Alternatively, two or three commercially available enzymes are used for processing organic materials into food products. In one preferred embodiment, neutrase is followed by termamyl treatment. In another preferred embodiment, viscozyme is followed by neutrase and possibly further followed by termamyl treatment. Still alternatively, functionally similar enzymes (i.e., enzymes in the same class with a similar specificity at approximately the same temperature and pH, and readily available to industry) can be used for processing organic materials into food products. Besides Neutrase (Novozymes North America, Inc.), examples of proteases include Multifect Neutral (Genencor International, Inc.), Fungal Protease Concentrate (Genencor Endo/Exo-Peptidase Complex), and Genencor Protease 899 (Genencor International, Inc.). Besides Termamyl (Novozymes North America Inc.), examples of alpha-amylase include BAN (Novozymes North America Inc.) and Fungamyl (Novozymes North America Inc.). Examples of glycosidase include Viscozyme, Celluclast, and Pectinax Ultra SP. Using the example of amaranth grain seed, the conventional method for producing amaranth seed milk gives a product with protein content of 5-6% (on a dry matter basis), whereas the present method increases the protein content to up to 15% (on a dry matter basis) with good functional and dietary properties.

There is provided a process for solubilizing an organic material in an aqueous solution. This process advantageously includes treating the organic material with a protease at a temperature effective to maintain the protease active; modifying the temperature to a level effective to deactivate the protease; treating the organic material with an alpha-amylase, the alpha-amylase being effective at the modified temperature; and modifying the temperature to a level effective to deactivate the alpha-amylase. This process is beneficial for organic materials high in starch (e.g., grains). Examples of the grain include amaranth, corn, oats, wheat, barley, rye, kamut, quinoa, rice, spelt, millet, triticale, sorghum, and combinations thereof.

Preferably, the organic material is processed prior to protease treatment by physically reducing the size of the material. The size reduction is preferably obtained by crushing, grinding, hammer milling, ball milling, crimping, blending, pressing, flaking, cracking, mixing or combinations thereof.

Still preferably, the organic material is defatted prior to protease treatment. Defatting is preferably performed by solvent extraction, pressing, expelling, extrusion, hot water extraction, carbon dioxide extraction, or combinations thereof.

Still preferably, the protease is neutrase, and the alpha-amylase is termamyl. A preferred embodiment includes subjecting the organic material to neutrase at about 40-50° C. for about 30-90 minutes followed by treatment with termamyl at about 90-100° C. for around 30-90 minutes. A more particularly preferred embodiment includes the usage of neutrase at about 45° C. for around 30 minutes followed by termamyl at about 95° C. for around 30-60 minutes.

This process can also be used for processing an organic material being a blend of oilseed and grain material. As a result, the solubilized organic material contains highly digestible protein and soluble starch fraction.

There is provided another process for solubilizing an organic material in an aqueous solution. This process advantageously includes treating the organic material with a glycosidase at a pH and a temperature effective to maintain the glycosidase active; modifying the pH to a level effective to deactivate the glycosidase; treating the organic material with a protease, the protease being effective at the modified pH; and modifying the temperature to a level effective to deactivate the protease. This process is beneficial for organic materials low in starch but high in muscilage, such as a seed or oilseed material. Representative examples of oilseed include flaxseed, soybean, linseed, chia seed, mustard seed, psyllium seed, quince seed, fenugreek seed, plantain seeds, and combinations thereof.

Preferably, the organic material is processed prior to protease treatment by physically reducing the size of the material. The size reduction is preferably obtained by crushing, grinding, hammer milling, ball milling, crimping, blending, pressing, flaking, cracking, mixing or combinations thereof.

Still preferably, the organic material is defatted prior to protease treatment. Defatting is preferably performed by solvent extraction, pressing, expelling, extrusion, hot water extraction, carbon dioxide extraction, or combinations thereof.

Still preferably, the glycosidase is viscozyme, and the protease is neutrase. A preferred embodiment includes subjecting the organic material to viscozyme at a pH range of from about 3.5 to about 5.5 at about 40-50° C. for about 0.5 to 6 hours followed by treatment with neutrase at a pH range of from about 5.6 to about 7.5 at about 40-50° C. for about 30-90 minutes. A more particularly preferred embodiment includes the usage of viscozyme at a pH of about 4.5 at about 45° C. for about 3 hours followed by neutrase treatment at a pH of about 6.0 at about 45° C. for about 60 minutes.

Still preferably, the pH is modified using a food grade acid such as citric acid, phosphoric acid, hydrochloric acid, acetic acid, lactic acid, octanoic acid, proprionic acid, or a mixture thereof. As a result of this process, the solubilized organic material contains highly digestible protein and soluble saccharide fraction.

There is provided still another process for solubilizing an organic material in an aqueous solution. This process advantageously includes treating the organic material with a glycosidase at a pH and a temperature effective to maintain the glycosidase active; modifying the pH to a level effective to deactivate the glycosidase; treating the organic material with a protease, the protease being effective at the modified pH; modifying the temperature to a level effective to deactivate the protease; treating the organic material with an alpha-amylase, the alpha-amylase being effective at the modified temperature and pH; and further modifying the temperature to a level effective to deactivate the alpha-amylase. This process is beneficial for organic materials high in both starch and muscilage, such as a blend of grains, seeds, oilseeds, or crop materials.

Preferably, the organic material is processed prior to protease treatment by physically reducing the size of the material. The size reduction is preferably obtained by crushing, grinding, hammer milling, ball milling, crimping, blending, pressing, flaking, cracking, mixing or combinations thereof.

Still preferably, the organic material is defatted prior to protease treatment. Defatting is preferably performed by solvent extraction, pressing, expelling, extrusion, hot water extraction, carbon dioxide extraction, or combinations thereof.

Still preferably, the glycosidase is viscozyme, the protease is neutrase, and the alpha-amylase is termamyl. A preferred embodiment includes subjecting the organic material to viscozyme at a pH range of from about 3.5 to about 5.5 at about 40-50° C. for about 0.5 to 6 hours followed by treatment with neutrase at a pH range of from about 5.6 to about 7.5 at about 40-50° C. for about 30-90 minutes and by treatment with termamyl at about 90-100° C. for around 30-90 minutes. A more particularly preferred embodiment includes the usage of viscozyme at a pH of about 4.5 at about 45° C. for about 3 hours followed by neutrase treatment at a pH of about 6.0 at about 45° C. for about 60 minutes and by termamyl at about 95° C. for around 30-60 minutes.

Still preferably, the pH is modified using a food grade acid such as citric acid, phosphoric acid, hydrochloric acid, acetic acid, lactic acid, octanoic acid, proprionic acid, or a mixture thereof. As a result of this process, the solubilized organic material contains highly digestible protein, soluble saccharide, and soluble starch fraction.

The following example is given for the purpose of illustrating various embodiments of the invention and is not meant to limit the present invention in any fashion.

EXAMPLE 1

Amaranth Grain Processing for Amaranth Protein-Starch Beverage Production

Amaranth grain seeds contain 11.5% moisture, 18.9% proteins, 2.8% ash, 10.2% ether extract and 56.6% carbohydrates with 14.2% dietary fiber. The seeds and some amaranth products are currently used as food products and ingredients, for example, some children use amaranth in their vegetable diet. To develop a new line of food products with broadened functional and dietary properties, amaranth meal with an oil content of less than 1% and moisture content of less than 10% was first mixed in deionized pure water at 60 rpm at a ratio of 5 parts water to 1 part meal by weight. Temperature was then increased to 45° C. quickly. Neutrase was added to the mixture at a ratio of 1 ml of enzyme to 50 grams of the starting meal weight. Mixing continued for about 30 min at 45° C. Termamyl was then added at a ratio of 1 ml of enzyme to 50 grams of the starting meal weight. The temperature was increased to 95° C. quickly to stop the action of the neutrase. The mixture was stirred for 30-60 min at 95° C. The product was cooled to room temperature to stop the activity of the termamyl. After cooling, the product was filtered through four layers of cheesecloth and spray dried with a maximum inlet temperature of 180° C., while the outlet temperature was kept at 100° C. FIG. 1 demonstrates this process. This process provides such new amaranth seed products as protein-starch beverages, diet protein candies, energy bars, breakfast cereals, beverage additives, infant formula ingredients, consumer coffee additives, snack food ingredients, protein supplements and fortifications for consumer and allergic populations, and other high quality protein products.

EXAMPLE 2

Flaxseed Processing for Flaxseed Protein Beverage Production

Figure 2:
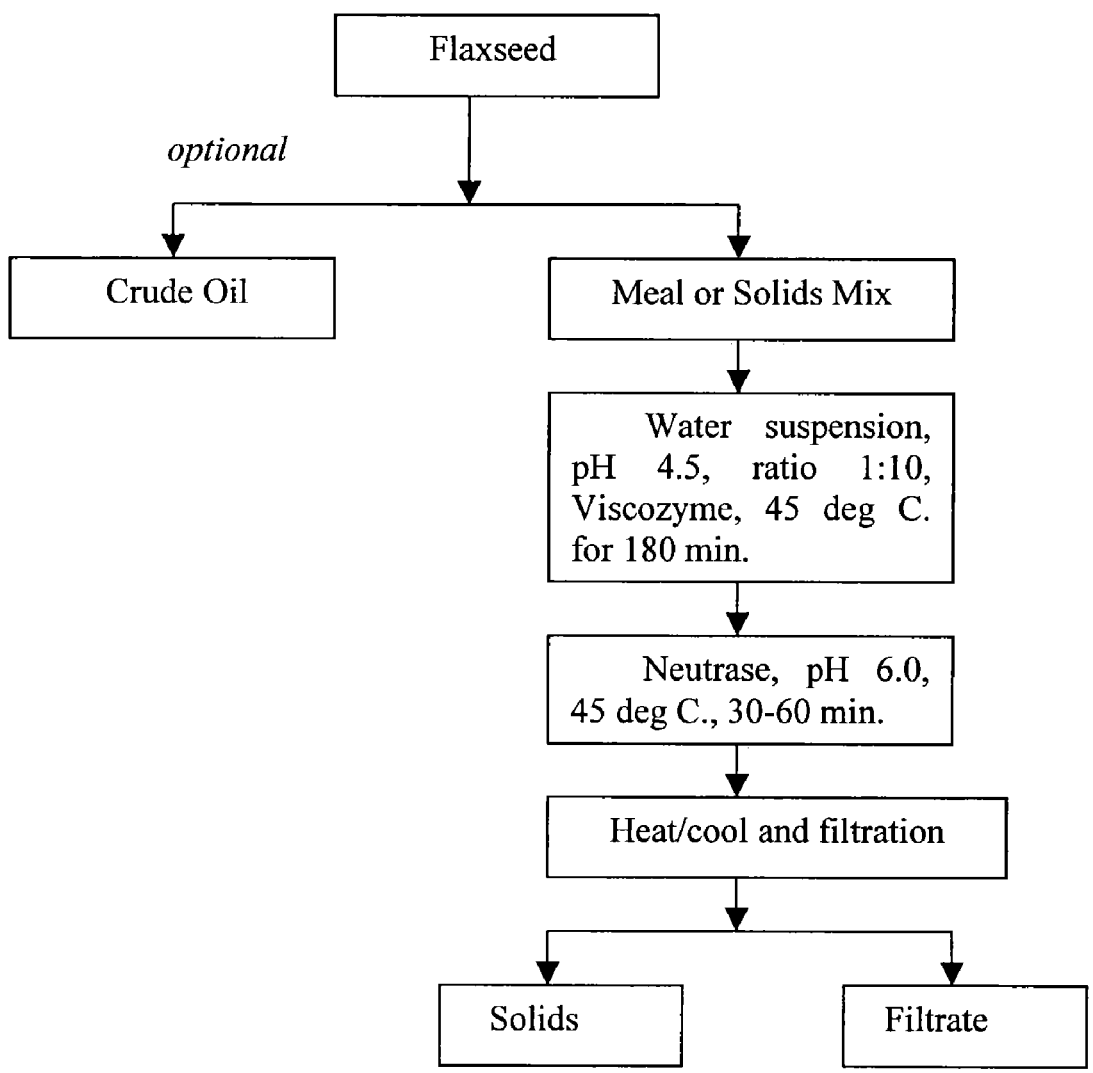
FIG. 2 is a flow chart demonstrating the method for processing oilseeds into highly soluble foods, feedstuffs and/or food ingredients according to the present invention.

Flaxseed, or linseed, contains 11.0% moisture, 20.0% proteins, 4.0% ash, 38.0% ether extract and 6.5% carbohydrates with 28.0% dietary fiber. The flax oil and flax flour are currently used as food products and ingredients. To develop a new line of products with broadened functional and dietary properties, ground flaxseed was first mixed in deionized pure water at 60 rpm at a ratio of 10 parts water to 1 part seed by weight and pH was adjusted to a 4.5 by 0.5 N HCl. Temperature was then increased to 45° C. quickly. Viscozyme was added to the mixture at a ratio of 1 ml of enzyme to 50 grams of the starting seed weight. Mixing continued for about 180 min. at 45° C. Then the pH was adjusted to 6.0. Neutrase was then added at a ratio of 1 ml of enzyme to 50 grams of the starting meal weight at a temperature of 45° C. for 60 minutes. The temperature was then increased to 95° C. quickly and held for 5 min. As a result, both enzymes were inactivated. The product was then cooled to room temperature. After cooling, the product was filtered through four layers of cheesecloth and spray dried with a maximum inlet temperature of 180° C., while the outlet temperature was kept at 100° C. FIG. 2 demonstrates this process. This process provides such new flaxseed products such as flaxseed milk, protein-starch beverages, diet protein candies, energy bars, breakfast cereals, beverage additives, infant formula ingredients, consumer coffee additives, snack food ingredients, protein supplements and fortifications, omega-3 fat formulations, and other high quality protein products.

EXAMPLE 3

Oat Bran Processing for Oat Bran Protein-Starch Beverage Production

Oat bran contains 6.5% moisture, 17.3% proteins, 2.9% ash, 7.0% ether extract and 66.2% carbohydrates with 2.2% dietary fiber. The bran and bran products are currently used as food products and ingredients. To develop a new line of food products with broadened functional and dietary properties, oat bran was first mixed in deionized pure water at 60 rpm at a ratio of 5 parts water to 1 part meal by weight. Temperature was then increased to 45° C. quickly. Neutrase was added to the mixture at a ratio of 1 ml of enzyme to 50 grams of the starting meal weight. Mixing continued for about 30 min at 45° C. Termamyl was then added at a ratio of 1 ml of enzyme to 50 grams of the starting meal weight. The temperature was increased to 95° C. quickly to stop the action of the neutrase. The mixture was stirred for 30 min at 95° C. The product was then cooled to room temperature to stop the activity of the termamyl. After cooling, the product was filtered through four layers of cheesecloth and spray dried with a maximum inlet temperature of 180° C., while the outlet temperature was kept at 100° C. FIG. 1 demonstrates the principles of this process. This process provides new oat bran products such as protein-starch beverages, diet protein candies, energy bars, breakfast cereals, beverage additives, infant formula ingredients, consumer coffee additives, snack food ingredients, protein supplements and fortifications, and other high quality protein products.

EXAMPLE 4

Oat Bran/Soybean Processing for Oat Bran/Soybean Protein-Starch Beverage Production Oat bran contains 6.5% moisture, 17.3% protein, 2.9% ash, 7.0% ether extract and 66.2% carbohydrates with 2.2% dietary fiber. Soybean contains 9.0% moisture, 30.2% protein, 5.0% ash, 19.6% ether extract and 30% carbohydrates with 15% dietary fiber. A mixture of 50/50 was used as the starting material. To develop a new line of food products with broadened functional and dietary properties this 50/50 material was first mixed in deionized pure water at 60 rpm at a ratio of 5 parts water to 1 part meal by weight. Temperature was then increased to 45° C. quickly. Neutrase was added to the mixture at a ratio of 1 ml of enzyme to 50 grams of the starting meal weight. Mixing continued for about 30 min at 45° C. Termamyl was then added at a ratio of 1ml of enzyme to 50 grams of the starting meal weight. The temperature was increased to 95° C. quickly to stop the action of the neutrase. The mixture was stirred for 30-60 min at 95° C. The product was then cooled to room temperature to stop the activity of the termamyl. After cooling, the product was filtered through four layers of cheesecloth and spray dried with a maximum inlet temperature of 180° C., while the outlet temperature was kept at 100° C. FIG. 1 demonstrates the principles of this process. This process provides such new oat bran/soybean products as protein-starch beverages, diet protein candies, energy bars, breakfast cereals, beverage additives, infant formula ingredients, consumer coffee additives, snack food ingredients, protein supplements and fortifications, and other high quality protein products.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

What is claimed is:

1. A process for solubilizing an organic material in an aqueous solution, the process comprising the steps of:
   (a) treating the organic material with an amount of glycosidase at a pH and a temperature effective to maintain the glycosidase active, wherein the organic material comprises a quantity of starch and mucilage, the amount of glycosidase being effective to digest polysacchardes;
   (b) modifying the pH to a level effective to deactivate the glycosidase;
   (c) treating the organic material with an amount of protease, the amount of protease being effective to break down proteins at the modified PH;
   (d) modifying the temperature to a level effective to deactivate the protease;
   (e) treating the organic material with an amount of alpha-amylase, the amount of alpha-amylase being effective to break down starch molecules at the modified temperature and pH; and
   (f) further modifying the temperature to a level effective to deactivate the alpha-amylase, thereby solubilizing the organic material.

2. The process of claim 1, wherein the organic material is a blend of grains, seeds, oilseeds, or crop materials.

3. The process of claim 1, where the organic material is processed prior to glycosidase treatment by physically reducing the size of the material.

4. The process of claim 3, wherein the size reduction is obtained by crushing, grinding, hammer milling, ball milling, crimping, blending, pressing, flaking, cracking, mixing or combinations thereof.

5. The process of claim 1, wherein the organic material is defatted prior to glycosidase treatment.

6. The process of claim 5, wherein defatting is performed by solvent extraction, pressing, expelling, extrusion, hot water extraction, carbon dioxide extraction, or combinations thereof.

7. The process of claim 1, wherein the glycosidase is viscozyme.

8. The process of claim 7, wherein viscozyme is mixed with the organic material at a pH range of from about 3.5 to about 5.5 at about 40-50° C. for about 0.5 to 6 hours.

9. The process of claim 8, wherein viscozyme is mixed with the organic material at a pH of about 4.5 at about 45° C. for about 3 hours.

10. The process of claim 1, wherein the protease is neutrase.

11. The process of claim 10, wherein neutrase is mixed with the glycosidase-treated organic material at a pH range of from about 5.6 to about 7.5 at 40-50° C. for about 30-90 minutes.

12. The process of claim 11, wherein neutrase is mixed with the glycosidase-treated organic material at a pH of about 6.0 at about 45° C. for about 60 minutes.

13. The process of claim 1, wherein the amylase is a termamyl.

14. The process of claim 13, wherein termamyl is mixed with the protease-treated organic material at about 90-100° C. for about 30-90 minutes.

15. The process of claim 14, wherein termamyl is mixed with the protease-treated organic material at about 95° C. for about 30-60 minutes.

16. The process of claim 1, wherein the pH is modified using a food grade acid.

17. The process of claim 16, wherein the food grade acid is selected from the group consisting essentially of citric acid, phosphoric acid, hydrochloric acid, acetic acid, lactic acid, octanoic acid, proprionic acid, and a mixture thereof.

18. The process of claim 1, wherein the solubilized organic material contains highly digestible protein, soluble saccharide, and soluble starch fraction.

* * * * *